(12) United States Patent
Finarov et al.

(10) Patent No.: US 6,213,952 B1
(45) Date of Patent: Apr. 10, 2001

(54) OPTICAL DEVICE FOR NON-INVASIVE MEASUREMENT OF BLOOD RELATED SIGNALS UTILIZING A FINGER HOLDER

(75) Inventors: Alexander Finarov; Yossie Kleinman; Ilya Fine, all of Rehovot (IL)

(73) Assignee: Orsense Ltd., Rahovot (IL)

( * ) Notice: Subject to any disclaimer, the term of this patent is extended or adjusted under 35 U.S.C. 154(b) by 0 days.

(21) Appl. No.: 09/407,390

(22) Filed: Sep. 28, 1999

(51) Int. Cl.⁷ .................................................. A61B 5/02
(52) U.S. Cl. ..................... 600/491; 600/310; 600/495; 600/322
(58) Field of Search ..................... 600/309–310, 600/345, 372, 479, 491, 499, 495, 500, 503, 322–324

(56) References Cited

U.S. PATENT DOCUMENTS

| | | | |
|---|---|---|---|
| 5,002,061 | * 3/1991 | Close et al. | 600/490 |
| 5,025,793 | * 6/1991 | Chin | 600/310 |
| 5,218,966 | * 6/1993 | Yamasawa | 600/490 |
| 5,313,940 | * 5/1994 | Fuse et al. | 600/310 |
| 5,511,546 | * 4/1996 | Hon | 600/490 |
| 5,638,816 | 6/1997 | Kiani-Azarbayjany et al. | 128/632 |
| 5,782,757 | 7/1998 | Diab et al. | 128/633 |
| 5,810,723 | 9/1998 | Aldrich | 600/310 |
| 5,860,919 | 1/1999 | Kiani-Azarbayjany et al. | 600/322 |
| 5,924,982 | * 7/1999 | Chin | 600/310 |

* cited by examiner

Primary Examiner—Cary O'Connor
Assistant Examiner—Ryan Carter
(74) Attorney, Agent, or Firm—Fitch, Even, Tabin & Flannery

(57) ABSTRACT

A finger holder for attaching to the patient's finger and an optical measurement device utilizing the finger holder for performing non-invasive measurements of blood-related signals are presented. The finger holder comprises a measuring unit located at a first location of the finger and a pressurizing assembly capable of applying desired over-systolic pressure to a second location on the patient's finger upstream of the first location with respect to a normal blood flow direction. The measuring unit is supported on a clip member that secures the fingertip between the clip's legs. A substantially rigid connector connects the clip member and the pressurizing assembly, wherein the connector engages the finger along its middle phalanx and proximal intephalangeal joint, thereby preventing it from folding during the measurements.

13 Claims, 2 Drawing Sheets

OPTICAL DEVICE FOR NON-INVASIVE MEASUREMENT OF BLOOD RELATED SIGNALS UTILIZING A FINGER HOLDER

FIELD OF THE INVENTION

This invention is generally in the field of non-invasive optical measurement techniques for measuring blood parameters and relates to an optical device for measuring blood-related parameters utilizing a finger holder.

BACKGROUND OF THE INVENTION

Non-invasive techniques for measurement of various blood parameters, such as blood oxygen saturation and the concentration of substances contained in the blood, have become very popular, since they advantageously do not require the withdrawal of a blood sample from a patient's body. Optical monitoring techniques of the kind specified typically utilize the detection of light transmitted or reflected from the location on the patient's body under measurement. Most of the known techniques utilize a measurement optical device or probe, designed in a manner to be attached to the patient's finger, which includes an optical assembly for irradiating the finger with light and detecting its light response.

U.S. Pat. No. 5,810,723 discloses an apparatus for the non-invasive monitoring of a patient's carboxyhemoglobin level. The patient breathes oxygen to saturate his blood hemoglobin prior to detection. The apparatus utilizes a clamp with arms which hold the patient's finger: one arm supports a light emitting source and the other supports a detector. A microprocessor controls the measurements and processes the detected signals.

U.S. Pat. No. 5,638,816 and its continuation, U.S. Pat. No. 5,860,919, disclose an apparatus for the non-invasive monitoring of blood parameters by applying pressure to the patient's finger, thus inducing an active pulse therein. The induced change of blood volume enables a better signal-to-noise ratio to be obtained.

U.S. Pat. No. 5,782,757 discloses a measuring devices in the form of disposable, folded adhesive sensors with optics embedded therein. The probe is designed so as to fit comfortably onto a patient's fingertip.

All the conventional devices of the kind specified are aimed at measuring enhanced optical pulsatile signals caused by the changes in the volume of the blood containing medium (finger). It is known that a regular optical pulsatile signal is typically 2–3% of the total transmission. The above devices are capable of obtaining the enhanced pulsatile signal that reach 8–10% of the total light transmission intensity. This enhancement of the natural pulsatile signal is a boundary of all conventional techniques of the kind specified.

A different technique is disclosed in co-pending application PCT/IL 99/00331, assigned to the assignee of the present application, where the measured signals are not pulsatile. This is an occlusion based technique, according to which a state of blood cessation is created in a medium under measurement and measurements are taken during this state. This enables to obtain significantly enhanced light response of the medium, as compared to that of the previously described techniques dealing with the pulsatile signals. To create such a state of blood cessation, over-systolic pressure should be applied to the patient's finger at either location upstream of the area under measurement, with respect to the direction of normal blood flow. None of the conventional probes is suitable for this purposes.

SUMMARY OF THE INVENTION

There is accordingly a need in the art to further improve non-invasive measurements of blood parameters, by providing a novel optical measurement device utilizing a finger holder.

It is a major feature of the present invention to provide such a device which is capable of providing the desired substantially stationary position of the finger during measurement, whilst applying over-systolic pressure to the finger.

It is a further feature of the present invention to provide such a device whose dimensions are adjustable to the finger of a specific patient.

The present invention takes advantage of the fact that measurements taken during the state of blood cessation allow for a significant increase of the blood-related signals, as compared to those taken during the state of normal blood flow. The main idea of the present invention is based on the following. To create a state of blood cessation within a patient's organ, over-systolic pressure should be applied thereto. Measurements are taken at a location downstream of that where the over-systolic pressure was applied with respect to the direction of normal blood flow. The measurement device, according to the invention, utilizes a finger holder coupled to a control unit. The finger includes a measurement unit and pressurizing assembly, which are spaced-apart from each other and are coupled to each other through a substantially rigid connector engaging the finger along its middle phalanx and proximal intephalangeal joint.

The provision of the rigid connector is associated with the following. The occlusion-based measurements are non-volumetric, the changes in volume of blood in the finger portion under measurements being undesirable for such measurements. However, it is a natural tendency of the finger under pressure to fold at the proximal intephalangeal joint, thereby causing undesirable changes in blood volume. By providing a substantially rigid support for the finger at the region of the middle phalanx during measurement, such undesirable folding can be avoided.

Generally, the measurement device may be associated with any other suitable patient's organ, such as his hand or wrist. If the patient's hand is considered, the rigid connector engages the patient's arm to prevent its folding at the elbow joint. It is more practical, however, to apply the device to the patient's finger.

The measurement unit is mounted in a clip member that secures the fingertip between its legs (either one pair or two pairs of legs). The provision of two pairs of legs advantageously enables to provide four-sided support for the finger, thereby preventing its folding at the distal phalanx.

There is thus provided according to the invention, a finger holder to be used in an optical measurement device for the non-invasive measurement of blood parameters, the finger holder comprising:

a clip member for securing the fingertip between its legs and supporting a measuring unit having an illumination-detection assembly for illuminating a first location of the finger, detecting light response of the illuminated location and generating data representative thereof;

a pressurizing assembly capable of applying desired over-systolic pressure to a second location on the patient's finger upstream of said first location with respect to a normal blood flow direction; and a substantially rigid connector between the clip member and the pressurizing assembly, the connector being adapted to engage the finger along its middle phalanx and proximal intephalangeal joint, thereby preventing it from folding during measurements.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
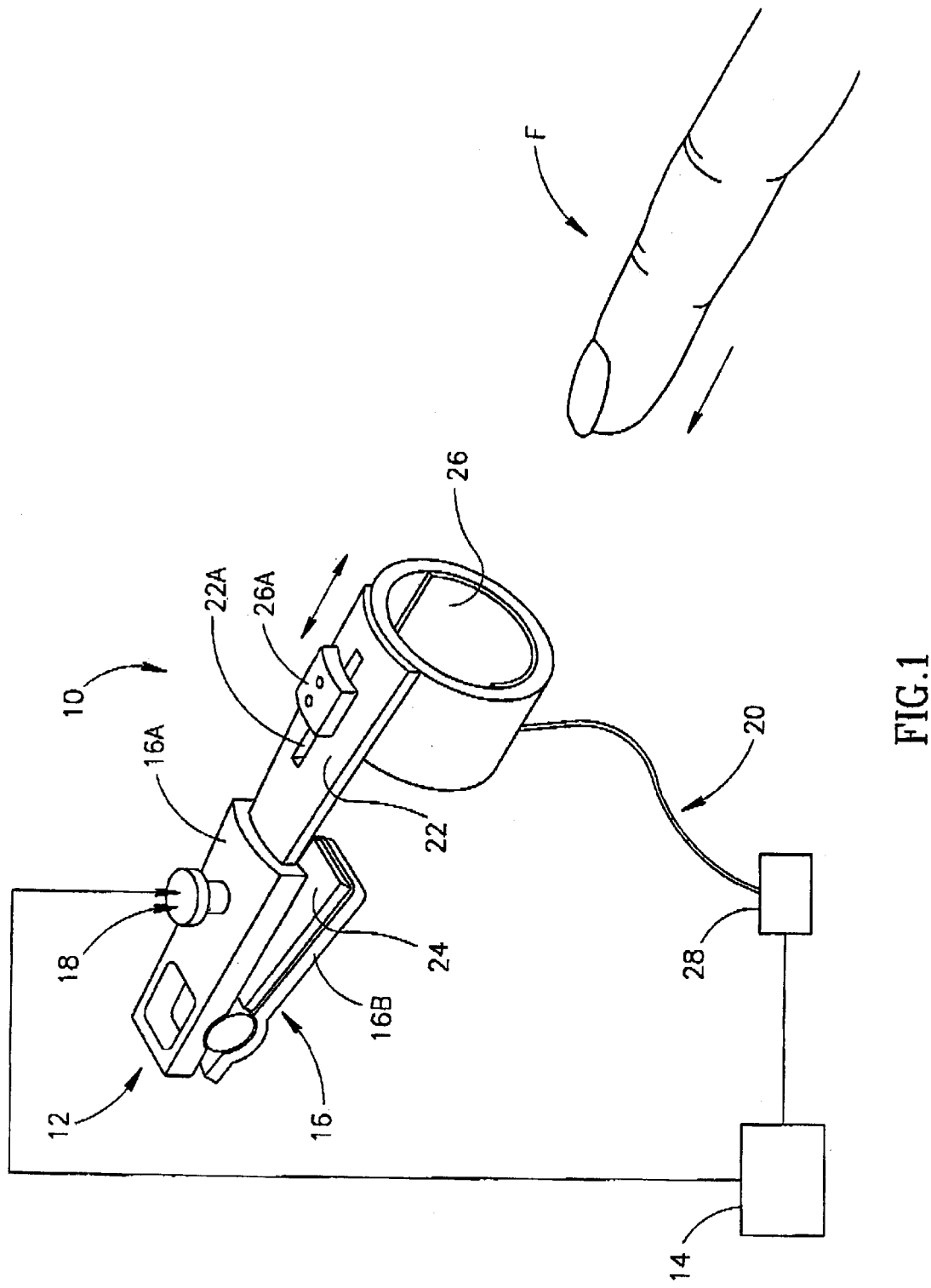
FIG. 1 is a schematic illustration of a device for non-invasive measurement of patient's blood parameters utilizing a finger holder constructed according to one embodiment of the invention.

Referring to FIG. 1, there is illustrated a measurement device, generally designated 10, for the non-invasive measurement of patient's blood parameters, such as oxygen saturation, blood pressure or the concentration of various substances, such as hemoglobin, glucose, cholesterol and other analyte concentrations. The device 10 includes a finger bolder 12 to be mounted on a patient's finger F, and a control unit 14 coupled to the finger holder either through wires or wireless. The finger holder 12 includes a clip member 16 with a measuring unit 18 installed therein, a pressurizing assembly 20 and a substantially rigid connector 22.

In the present example, the clip member 16 is a two-legged member for securing the patient's finger F between its legs 16A and 16B that engage the finger F at both its top and bottom, respectively. A flexible thermoconductive pad 24, made, for example, of rubber or silicone, is provided at the inner surfaces of the legs 16A and 16B. The pad 24 is coupled to a power source (not shown) which is operated by the control unit 14 for applying appropriate, substantially low voltages, for example in the range 1V–24V to the pad 24, enabling heating of the finger portion located between the clip legs 16A and 16B (i.e., the location under measurements) up to 37–38° C. The heating ability of the device increases the accuracy of the non-invasively derived blood-related parameters. The substantially low voltage supply is, on the one hand, acceptable for medical devices, and, on the other hand, requires low power supply (e.g., 6–9V) that allows for using batteries, thereby rendering the entire device conveniently portable.

The measuring unit 18, which is partly shown in the figure, does not form part of the present invention, and therefore need not be specifically illustrated and described, except to note the following. The measuring unit 18 comprises both an illumination and detection means that could be accommodated either at one side of the finger when operating in a reflection mode, or at opposite sides of the finger when operating in a transmission mode. These reflected or transmitted signals present light response of the finger to incident radiation. In the present example, the measuring unit 18 provides illumination of the finger F with at least two different wavelengths, and detects light transmitted therethrough. Data indicative of the detected light is transmitted to the control unit 14, that includes a processor operated by a suitable software model for determining and analyzing the time dependency of the detected light for each incident wavelength to calculate the desired parameter of blood.

As indicated above, the present invention utilizes the measurement of blood-related signals at a state of substantial blood cessation. To this end, the pressurizing assembly 20 is capable of applying over-systolic pressure, e.g., 270–300 mmHg (generally, adjustable for each specific patient) at a location upstream of the measuring unit 18 with respect to the direction of normal blood flow. The pressurizing assembly 20 includes an air cushion cuff 26 in the form of a ring wrapping the respective location on the patient's finger F, and a pneumatic drive 28 coupled to the cuff 26 and to the control unit 14.

Hence, the drive 28, whilst being actuated by the control unit 14, operates to apply over-systolic pressure to the finger portion underneath the cuff-ring 26. The application of pressure is maintained for a period of time so as not to cause irreversible changes in the finger, e.g., 4 seconds. Then, the control unit operates the drive 28 to release the pressure. The effective measurements, i.e., the results which have to be analyzed, are those taken at the state of blood cessation, as will be described more specifically further below.

As clearly seen in FIG. 1, the connector 22 is shaped like a plate, and is formed with an elongated slot 22A. The cuff-ring 26 is formed with a projection 26A installed in the slot 22A for reciprocating sliding movement along its axis. This enables to adjust the length of the finger bolder 12 to that of the finger of a specific patient. The rigid plate-like connector 22 engages the finger along its middle phalanx, preventing its folding at the proximal intephalangeal joint, thereby avoiding undesirable changes in blood volume.

The operational mode of the device 10 may be such that the control unit 14 actuates the measuring unit 18 for performing continuous measurements starting prior to the application of over-systolic pressure. In this case, only those signals which are associated with the state of blood cessation are taken into consideration. Measurements taken during the time period prior to the establishment of this state should be disregarded, due to the unavoidable influence of motional and/or other artifacts causing non-monotonic fluctuations of the light transmission. According to an alternative operational mode of the device 10, the control unit 14 actuates the measuring unit 18 approximately 0.5 sec after the application of the over-systolic pressure. During the time period corresponding to the existence of the state of blood cessation, relative light transmission of blood is observed, which reaches its maximum and may last for about 2–5.5 sec (generally, from one second to several minutes).

To obtain meaningful results, either one of at least two timely separated measurement sessions should be considered, at least one of them occurring during the state of blood cessation, or a single long continuous measurement session is considered starting after the establishment of the state of blood cessation. During the first measurement session, the control unit 14 operates to maintain the cuff 26 in its squeezed position. The control unit 14 then operates the pressurizing assembly 20 to release the over-systolic pressure. The squeezing action of the cuff 26 is ceased, and after a short delay of about 0.5 sec, the blood flow gradually increases during approximately 5 sec. Then, the control unit 14 actuates the second measurement session at a state of the transitional blood flow. The illumination unit continues to illuminate the finger, but squeezing is halted. The detection unit, being synchronized by the control unit 14, detects the light response of the finger.

In other words, the control unit 14 selectively operates the measuring unit 18 and the pressurizing assembly 20, and analyzes data coming from the measuring unit. The construction and operation of the control unit do not form part of the present invention, and may be of any known kind capable of running an appropriate software model.

Figure 2:
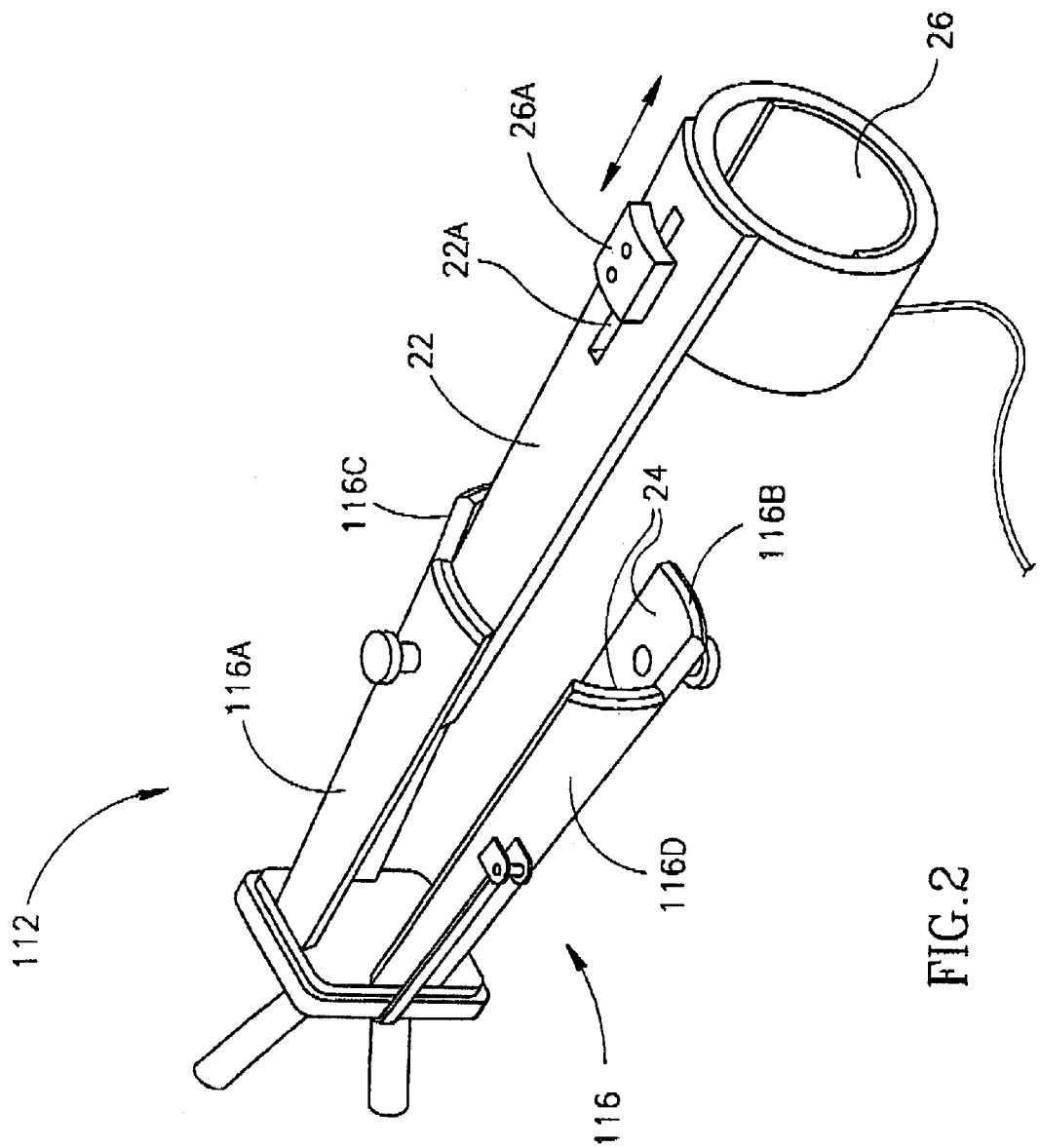
FIG. 2 illustrates another embodiment of the finger.

Reference is made to FIG. 2 illustrating a finger holder 112 having somewhat different construction of its clip member 116, as compared to that of the finger holder 12. The clip member 116 is a four-leg member, wherein two opposite legs 116A and 116B engage the finger at its top and bottom thereof, and the other opposite legs 116C and 116D engage the opposite sides of the finger, respectively. Such four-sided support of the fingertip prevents its folding at the distal phalanx, thereby avoiding undesirable blood volume changes.

It should be noted that the connector 22 may be located at either side of the patient's finger. Alternatively, a pair of such connectors can be used located at opposite sides of the finger. Additionally, the processor may be accommodated within the cuff, and the wires, if any, connecting the processor to the output circuit of the measuring unit, may pass through the rigid connector.

Those skilled in the art will readily appreciate that various modifications and changes may be applied to the preferred embodiments of the invention as herein before exemplified without departing from its scope defined in and by the appended claims. For example, the cuff 26 may be a band formed with Velcro-like fasteners, so as to form a ring wrapping the patient's finger when in the operational position of the device. Alternatively, a band composed of a set of various air cushions pressuring on the finger. In this case, the pressurizing assembly fits itself to each finger size without any additional adjusting means.

What is claimed is:

1. A finger holder to be used in an optical measurement device for non-invasive measurement of blood parameters, the finger holder comprising:
   a clip member for securing a fingertip between its legs and supporting a measuring unit having an illumination-detection assembly for illuminating a first location of a finger, detecting light response of the illuminated location and generating data representative thereof;
   a pressurizing assembly capable of applying desired over-systolic pressure to a second location on the finger upstream of said first location with respect to a normal blood flow direction; and
   a substantially rigid connector between the clip member and the pressurizing assembly, the connector being adapted to engage the finger along its middle phalanx and proximal intephalangeal joint, thereby preventing it from folding during the measurements.

2. The finger holder according to claim 1, wherein said clip member has two clamping legs for securing the finger therebetween in a manner allowing the optical measurements.

3. The finger holder according to claim 1, wherein said clip member is provided at an inner surface thereof with a flexible member for wrapping the first location of the finger.

4. The finger holder according to claim 3, wherein said flexible member is made of a thermoconductive material for heating said first location under measurements up to a desired temperature.

5. The finger holder according to claim 4, wherein said desired temperature is approximately 37°–38° C.

6. The finger holder according to claim 4, wherein the flexible thermoconductive material is rubber.

7. The finger holder according to claim 4, wherein the flexible thermoconductive material is silicone.

8. The finger holder according to claim 1, wherein said pressurizing assembly comprises an air cushion cuff-ring wrapping said second location, and a pneumatic drive coupled to the cuff-ring so as to apply said over-systolic pressure to said second location.

9. The device according to claim 8, wherein said connector is shaped like a plate and has an elongated slot extending the finger's axis, said cuff-ring having a projection installed in the slot for sliding movement along the slot's axis.

10. The finger holder according to claim 8, wherein said cuff-ring is a band having hook and loop fasteners so as to form the ring on the patient's finger.

11. The finger holder according to claim 1, wherein said over-systolic pressure is such as to create a state of substantial blood cessation within said second region.

12. The finger holder according to claim 11, wherein said over-systolic pressure is in the range 270–300 mmHg.

13. An optical measurement device for performing non-invasive measurement of blood-related signals, the device comprising a finger holder constructed according to claim 1, and a control unit coupled to the measuring unit and to a drive of the pressurizing assembly for selectively operating them and analyzing data coming from the measuring unit.

* * * * *